US005111048A

United States Patent [19]
Devitt et al.

[11] Patent Number: 5,111,048
[45] Date of Patent: May 5, 1992

[54] APPARATUS AND METHOD FOR DETECTING FATIGUE CRACKS USING INFRARED THERMOGRAPHY

[75] Inventors: John W. Devitt, Loveland; Thomas E. Bantel, Cincinnati, both of Ohio; Joseph M. Sparks, Newport, Ky.; Janet S. Kania, Cincinnati, Ohio

[73] Assignee: General Electric Company, Cincinnati, Ohio

[21] Appl. No.: 588,909

[22] Filed: Sep. 27, 1990

[51] Int. Cl.⁵ ............................................. G01N 21/71
[52] U.S. Cl. ...................................... 250/342; 374/5; 250/341
[58] Field of Search ............... 374/5, 4; 250/341, 342, 250/330

[56] References Cited

U.S. PATENT DOCUMENTS

| | | | |
|---|---|---|---|
| Re. 32,166 | 6/1986 | Berge | 51/322 |
| 3,020,745 | 2/1962 | Sielicki | 73/15 |
| 3,206,603 | 9/1965 | Mauro | 250/83.3 |
| 3,222,917 | 12/1965 | Roth | 73/15 |
| 3,401,551 | 9/1968 | Maley | 73/15 |
| 3,427,861 | 2/1969 | Maley | 73/15 |
| 3,433,052 | 3/1969 | Maley | 73/15 |
| 3,434,332 | 3/1969 | Maley | 73/15 |
| 3,451,254 | 6/1969 | Maley | 73/15 |
| 3,462,602 | 8/1969 | Apple | 250/83.3 |
| 3,499,153 | 3/1970 | Stanfill III. | 250/83.3 |
| 3,808,439 | 4/1974 | Renius | 250/334 |
| 4,109,508 | 8/1978 | Fukuyama | 73/15 |
| 4,232,554 | 11/1980 | Aleck | 73/577 |
| 4,481,418 | 11/1984 | Vanzetti et al. | 250/347 |
| 4,562,736 | 1/1986 | Iwasaki et al. | 73/587 |
| 4,647,220 | 3/1987 | Adams et al. | 374/5 |
| 4,965,451 | 10/1990 | Sölter | 250/341 |

OTHER PUBLICATIONS

Thermal & Infrared Nondestructive Testing of Composites and Ceramics Donald R. Green *Materials Evaluation* vol. 29, No. 11 (Nov. 1971) pp. 241-247.

Primary Examiner—Carolyn E. Fields
Assistant Examiner—James E. Beyer
Attorney, Agent, or Firm—Charles L. Moore, Jr.; Jerome C. Squillaro

[57] ABSTRACT

A method and apparatus for detecting a defect in a workpiece are disclosed. The workpiece is positioned with a surface of the workpiece to be inspected in an optical path of an infrared radiation detector. A selected portion of the workpiece is heated by scanning with electromagnetic radiation for a selected duration to cause an increase in radiance from any defect present in the selected portion. Any defects, present in the workpiece selected portion, which may cause a failure of the workpiece, may be detected and distinguished from minor surface anomalies by analyzing a transient response of the irradiance received by the infrared radiation detector.

25 Claims, 3 Drawing Sheets

APPARATUS AND METHOD FOR DETECTING FATIGUE CRACKS USING INFRARED THERMOGRAPHY

The government has rights in this invention pursuant to Contract Nos. F33657-84C-0264 and F33657-84C-2011 awarded by the Department of the Air Force.

BACKGROUND OF THE INVENTION

The present invention relates to the detection of fatigue cracks or defects in materials and, more particularly, to an apparatus and method for detecting fatigue cracks in gas turbine engine components and airframe components, such as fuselages, wing assemblies, tail sections and the like, by using infrared thermography.

Fatigue cracks occur in a wide variety of both metallic and nonmetallic aircraft parts. Low cycle fatigue (LCF) cracks represent one of the most prevalent failure mechanisms for material that has any cyclic stresses applied to it. This is particularly true for any of the rotating parts in a gas turbine engine. At the same time LCF cracks are a difficult type of material defect to detect. Many methods of detection are employed within the aircraft industry in an attempt to consistently locate LCF cracks early in their growth to preclude a material failure.

Currently used nondestructive evaluation (NDE) methods for inspecting aircraft parts and gas turbine engine components for fatigue cracks or other defects, which could cause a failure of the engine or airframe, include surface wave ultrasonic testing, eddy current testing, acoustic emission evaluation and fluorescent penetrant inspection. Each of these methods is not without certain limitations and disadvantages; some methods require that the evaluation instrumentation contact the surface. Unique geometries of some components may restrict the evaluation techniques that can be utilized, and some of these methods are susceptible to errors and false indications from contaminants on the surface of the component being inspected or contaminants within the cracks or defects. Some NDE methods are susceptible to errors or false indications of the presence of a defect from surface roughness and other surface anomalies which do not result in a failure.

Generally, none of the above-described NDE methods is considered to be singularly capable of detecting LCF cracks with sufficient reliability and ease of application to have emerged as a preferred method. In the most critical of applications, two or more of these conventional methods are typically used in tandem as a crosscheck on one another.

Infrared methods of NDE overcome many of the aforementioned disadvantages associated with the NDE methods listed above. Infrared methods can be performed relatively quickly and easily and are also suitable for adaptation to automation without many of the limitations associated with the other NDE methods described above.

Infrared NDE methods operate on the premise that all matter continuously absorbs and emits electromagnetic radiation. The continual motion of the charged particles within a material results in the emission of electromagnetic radiation. The motion of the charged particles will increase with an increase in temperature and therefore the continuous emission of radiation from the material will also increase with an increase in temperature. The Stefan-Boltzman law states that the total energy radiated by a perfect black body is proportional to the fourth power of the absolute temperature. The ratio of the total emissive power of any body to that of a perfect black body at the same temperature is known as the emissivity of the body and is numerically equal to the absorptivity of the body. Cracks and defects may be detected because they will typically absorb more radiation and therefore have a higher emissivity and radiance relative to the relatively flat and smoother surface areas surrounding the defect.

A thermal imaging device for nondestructive testing using laser illumination and an infrared detector is disclosed in U.S. Pat. No. 3,808,439 issued to Renius. Renius teaches continuously scanning the entire surface of a specimen under test with a $CO_2$ laser beam so that the amount of total incident radiation absorbed by the specimen is equal for the entire surface. The laser scanning causes an increase in the surface temperature with the heat propagating through the specimen. The differences in the heat transferred through different portions of the specimen are detected by an infrared detector and are then used to determine subsurface voids or defects.

Another NDE device and method using infrared radiation is disclosed in U.S. Pat. No. 3,499,153 issued to Stanfill. This invention detects flaws or inhomogeneities in the surface of a material under test by irradiating the material surface with infrared radiation to maintain the material at a substantially uniform temperature. Radiation reflected by the material is then detected by a radiometer.

A further method for detecting flaws in the surface of a tested material by detecting thermal emission from the material is disclosed in U.S. Pat. No. 4,232,554; this invention loads or places the part being tested under a uniform tensile stress normal to the crack and then detects thermal emission signals indicative of plastic deformation. The presence of a crack or deformity can then be determined from the thermal emission signals.

Other NDE devices and methods are disclosed in U.S. Pat. Nos. 3,462,602; 3,451,254; 3,206,603; 3,222,917; 3,434,332; 3,433,052; 3,427,861 and 3,401,551.

None of the above-referenced patents disclose the benefits derived by selective, localized electromagnetic radiative heating to improve the contrast between any crack, or defect, and the material surrounding the crack to improve the detection ability of very minute cracks, as small as about 0.01 inches in length. Additionally, there is no teaching in any of the above-referenced patents of the benefits derived from analyzing a transient response corresponding to a detected infrared image of the radiance from a selectively heated workpiece surface, to distinguish between defects which could result in a failure and other minor surface anomalies which are not of great concern.

SUMMARY OF THE INVENTION

It is accordingly a primary object of the present invention to provide a novel method and apparatus for detecting a defect at the surface of an airframe component, gas turbine engine component or the like which is not subject to the foregoing disadvantages.

It is another object of the present invention to provide a more accurate method and apparatus for detecting defects at the surface of a component with fewer false indications than has heretofore been available.

It is a further object of the present invention to provide a method and apparatus for detecting defects which is not restricted by the geometry of the particular part under test, is less sensitive to the roughness of the surface of the part and is less susceptible to false indications from any contaminants that may be within the defect or on the part surface.

It is yet another object of the present invention to provide a novel apparatus and method for detecting a defect in a component which is efficient and easily incorporated in an automated system.

In accordance with the present invention, a method for detecting a defect in an aircraft component, gas turbine engine component or the like, includes the steps of: positioning a surface of the workpiece to be inspected in an optical path of an infrared radiation detector, such as an infrared radiometer, camera or the like; heating by electromagnetic radiation a selected, localized portion of the surface of the component for a selected duration to cause an increase in radiance from any defect present in the selected surface portion, the radiation detector operating primarily in a different spectral band than the heating electromagnetic radiation; detecting defects in the selected surface portion of the component by analyzing a transient response of the radiance received from any defect by the infrared radiation detector. Preferably, the optical path is substantially normal to a plane parallel to the workpiece selected portion.

In another embodiment of the present invention, a stress is applied to the component to cause any subsurface defects, which are proximate to the surface, to be detectable at the surface of the component. The stress applied has a stress intensity level or factor below a characteristic damage threshold stress intensity factor of the material from which the component is manufactured.

In accordance with the present invention, an apparatus for detecting a crack in a component includes a laser, for providing a laser beam, and optics for scanning the laser beam across a selected surface area of the component, to heat the selected surface area and to cause an increase in radiance from any defects present in the selected area. An infrared radiometer or camera is positioned in an optical path substantially parallel to the surface normal of the selected surface area, to receive the radiance from the selected surface area. The infared radiometer and radiometer controls generate a series of graphs corresponding to the radiance received from the selected surface area for a selected duration immediately after the heat is removed. The series of graphs provide a transient response of the radiance received. The transient response may be analyzed to distinguish between minor surface anomalies and a crack or defect which may cause a failure of the component.

The above-listed objects and other objects of the present invention, together with the features and advantages thereof, will become apparent from the following detailed specification when read with the accompanying drawings.

DETAILED DESCRIPTION OF THE PREFERRED EMBODIMENTS

Figure 1:
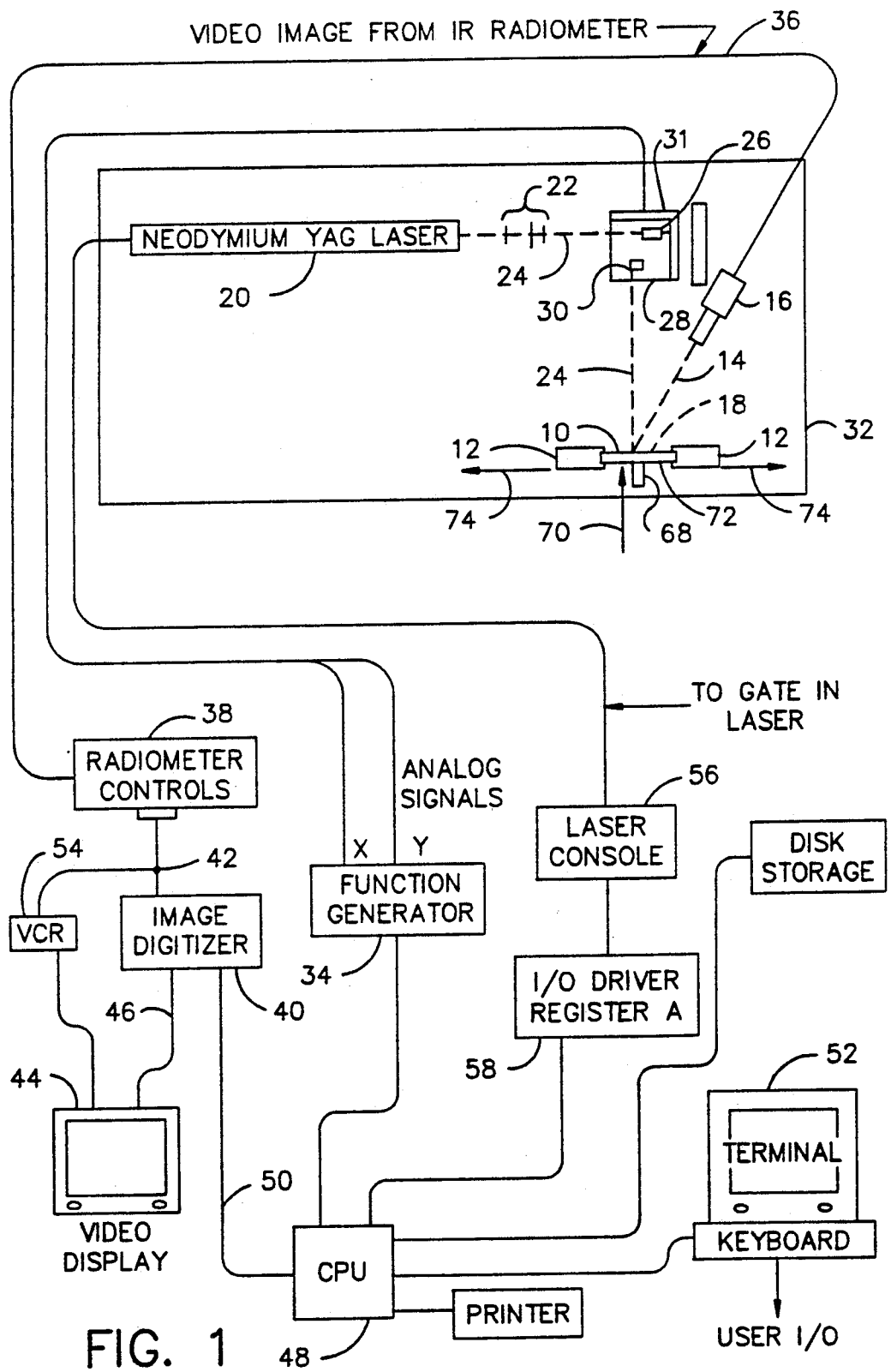
FIG. 1 is an illustration of a schematic the diagram of the nondestructive evaluation test setup in accordance with the present invention.

Referring initially to FIG. 1, a component 10, such as an aircraft component or a gas turbine engine component or the like, is mounted in a fixture 12 and positioned in an optical path 14 or within the field of view of a detector 16, such as an infrared radiometer, infrared camera or the like. Detector 16 may be a Model 210 or a Model 525 infrared imaging radiometer as manufactured by Inframetrics of Billerica, Mass. While optical path 14 of detector 16 is shown in FIG. 1 to intersect, at some angle, optical path 14 is preferably substantially parallel to the surface normal of selected surface 18 for optimum defect detection.

A laser 20 and focusing optics 22 provide a coherent laser beam 24 which is focused onto a first mirror 26 of a two-dimensional (2-D) scan mirror arrangement 28. Scan mirror arrangement 28 includes first mirror 26, a second mirror 30 and a scanning device 31, such as a piezoelectric device, galvanometer or the like, associated with each mirror for moving or scanning laser beam 24 across selected surface 18 of component 10 to selectively heat portions of surface 18. Fixture 12, detector/radiometer 16, laser 20 and 2-D scan mirror arrangement 28 are preferably mounted on an optical table within a safety enclosure, both of which are schematically represented in FIG. 1 by box 32 surrounding the aforementioned constituents.

Laser 20 is preferably a YAG laser operating at a wavelength of about 1.06 microns and IR radiometer or camera 16 preferably operates at a selected wavelength band between about 3 microns and about 12 microns so that radiometer 16 will not detect the laser light reflected by surface 18 and thereby give false indications of a defect when one is not present.

While a presently preferred embodiment utilizes scanning laser beam 24 to selectively heat portions of surface 18, other electromagnetic radiative (EMR) heating methods could be used as well, such as laser pulsing, flash lamps or the like. Whatever heating source is selected, the radiation detector and heating source should operate in different spectral bands to adequately distinguish between a defect and the surrounding material. If a broader band heating source is used that interferes with the detector 16, it may be necessary to view or detect radiation from selected surface 18 after the heating source has been removed.

A function generator 34 is provided to generate analog signals to scan mirror arrangement 28 for driving scanning devices 31. The energized scanning devices 31 will pivotally move first and second mirrors 26 and 30 to cause laser beam 24 to move in an X-y coordinate system, responsive to the analog signals received from function generator 34. In this manner, substantially the entire surface area of component 10 may be scanned by laser beam 24. Scan mirror arrangement 28 and function generator 34 are known constituents which may be interconnected as shown in FIG. 1.

Video signals from IR radiometer 16 are fed by a communications link 36 to a radiometer control 38 for adjusting the focus and contrast of IR radiometer 16. Radiometer control 38 is in turn connected to an image digitizer 40 by another communication link 42; image digitizer 40 is in turn interconnected to a video display 44 by a communications link 46 and is also connected to a central processing unit (CPU) 48 by a communications link 50. CPU 48 may be interfaced by a system operator through a keyboard and terminal combination 52.

Image digitizer 40 may be a "DIGIMAX" as manufactured by Dataqube, Inc. of Peabody, Mass. Image digitizer 40 facilitates storage by CPU 48 of a series of images of the radiance received from selected surface 18 for analysis of the transient response of the radiance as described in more detail hereinafter.

Computer software may be provided to enhance the digitized signal created from the video image provided by IR radiometer 16 to improve the detection ability of even the most minuscule of defects in component surface 18 as laser beam 24 is scanned across the surface. Defects as small as 0.01 inches in length have been successfully detected by the apparatus shown in FIG. 1 and even better results may be realized with computer enhancement.

A videocassette recorder (VCR) 54 may be interconnected between radiometer control 38 and video display 44 for recording the actual analog video image received by IR radiometer 16 as laser beam 24 scans across component surface 18. This recording may be used for further analysis of the video image, to distinguish between minor surface anomalies and defects which could result in failure of component 10.

Function generator 34 may also be interconnected to computer 48 so that the scanning of surface 18 by laser beam 24 may be preprogrammed or controlled by an operator through terminal 52.

Laser 20 is also interconnected to CPU 48 by a laser console 56 and an input/output (I/O) driver register A 58. The gating and power level of laser 20 may then be preprogrammed by CPU 48 or controlled by an operator via terminal 52. The laser power density should be sufficiently high to provide a good contrast between any defects and the material surrounding the defects, when surface area 18 is selectively heated by laser beam 24 and when radiometer 16 receives the radiance from surface 18, but the laser power must not be so high as to damage component 10.

Component surface 18 is preferably cleaned to lower the emissivity of the component surface under test and to remove coatings of any type, such as paints, thermal barrier coatings or the like that may occlude a defect. By cleaning, the detection ability of very minute defects is improved by enhancing the contrast between any defects and the surrounding material. After cleaning, component 10 may then be mounted in fixture 12 in alignment with 2-D scan mirror arrangement 28 and scanning infrared radiometer 16. Laser beam 24 is preferably incident upon selected surface 18 close to normal to the surface as possible for optimum defect detection.

Figure 2A:
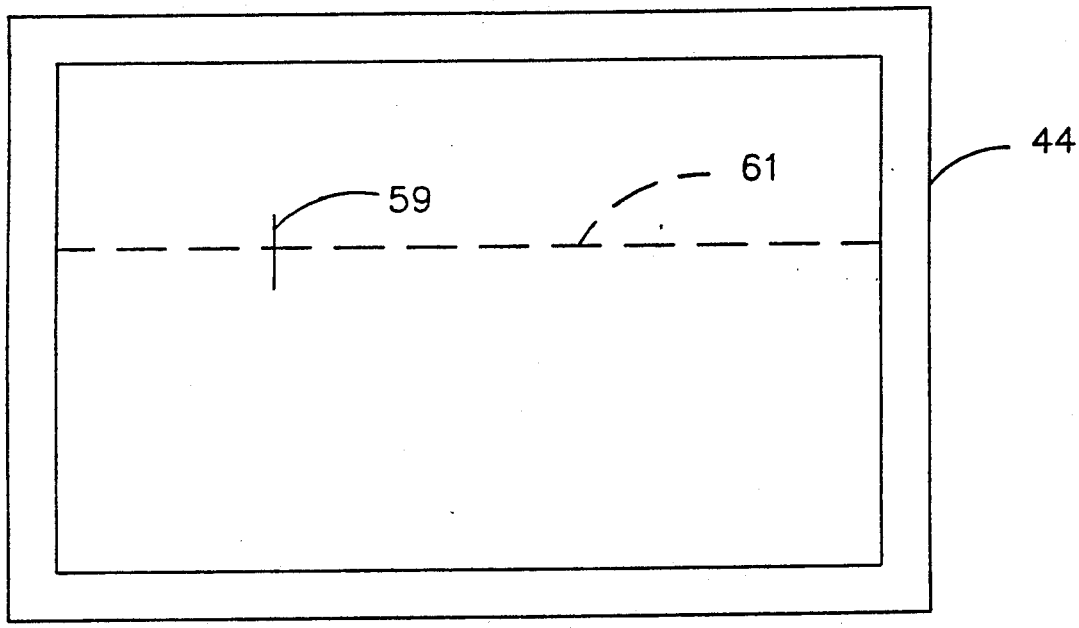
FIG. 2A is an illustration of a video image of a selected portion of a component under test in accordance with the present invention.
Figure 2B:
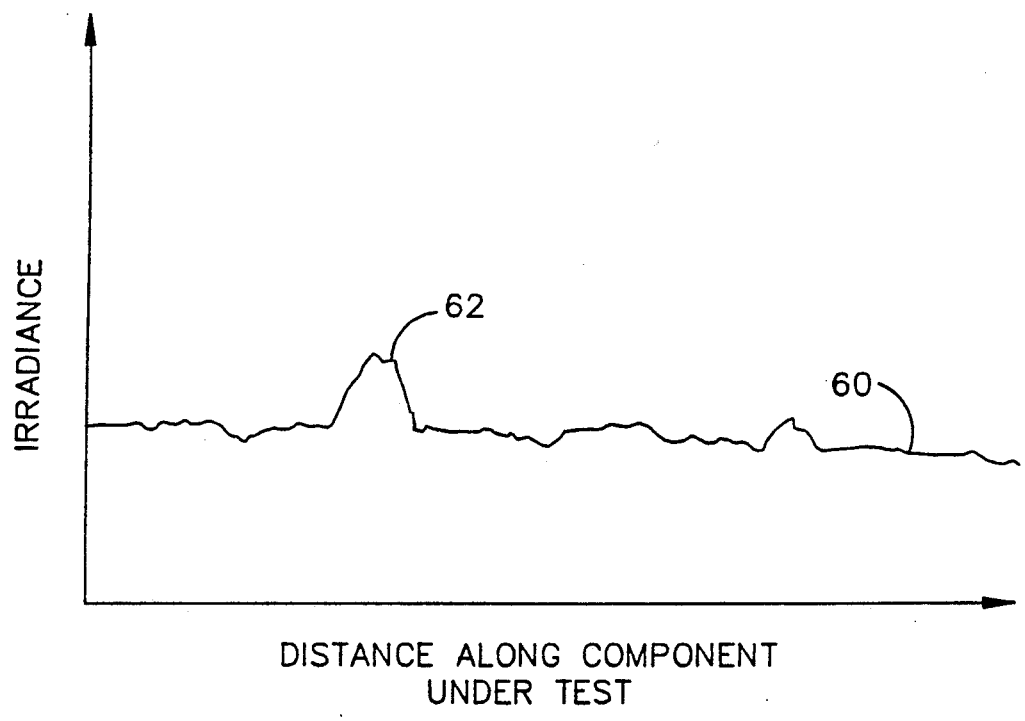
FIG. 2B is an illustration of a graph of the radiance from the selected portion shown in the infrared video image of FIG. 2A at a selected uniform temperature.
Figure 2C:
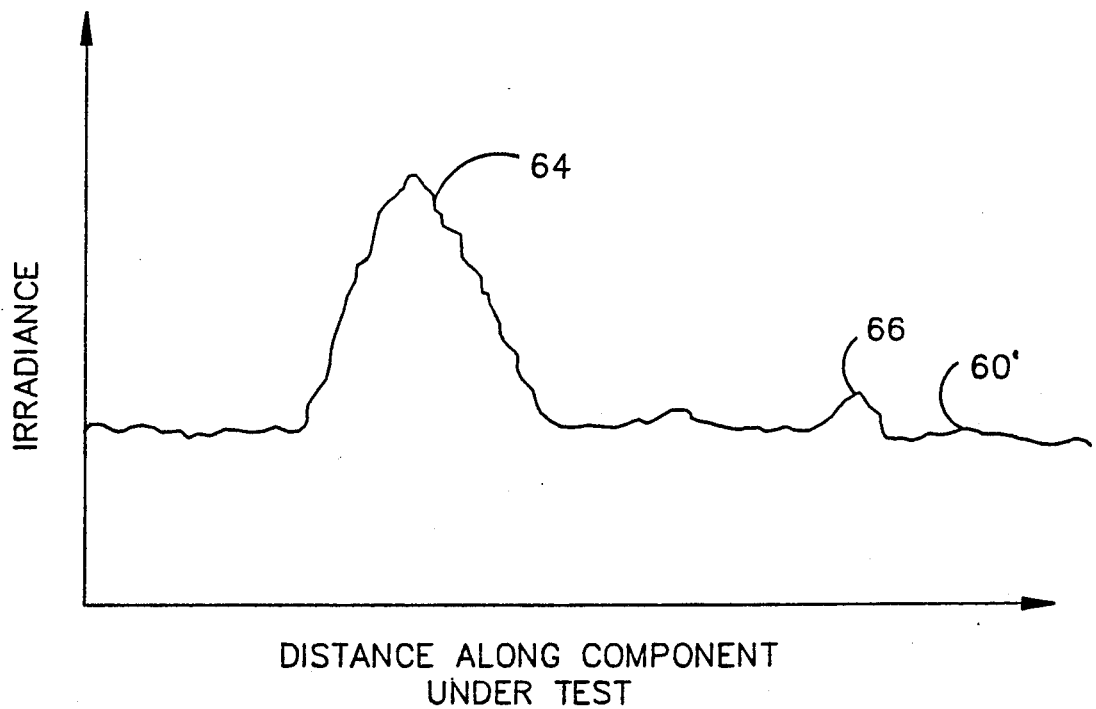
FIG. 2C is an illustration of a graph of the radiance from the selected portion shown in the infrared video image of FIG. 2A during scanning by a laser beam.

Selected surface 18 may be preheated by scanning with laser beam 24 or by other methods such as flash lamps, an oven or the like to provide an elevated, uniform temperature above ambient across selected surface 18. The uniform temperature may be between about 50° C. and about 150° C. A defect 59 will appear in a video image from radiometer 16 as illustrated in FIG. 2A. Radiometer 16 and radiometer controls 38 can also provide a graph 60, as illustrated in FIG. 2B, on video display 44 of the irradiance scanning along a selected line across a portion of selected surface 18. The selected line scanned by radiometer 16 is indicated by a cursor, illustrated by a broken line 61 in FIG. 2A. Thus the radiance received by radiometer 16 while scanning along surface area 18 can be measured at different locations on surface 18 by moving cursor 61 up and down the video display 44, and the intensities of a single horizontal scan across the video image can be displayed in graphical form. FIGS. 2B and 2C illustrate such scans that cross both a defect and some surface anomalies. Any defects along surface 18 will appear as a peak 62 as shown in the graph of FIG. 2B.

As laser beam 24 is scanned across preheated surface 18, selective, localized heating will occur as the beam passes. The radiance, as detected by radiometer 16 and converted to a graph 60' (FIG. 2C) on video display 44, will peak (as indicated by reference numeral 64 in FIG. 2C) as laser beam 24 passes over the defect because of the higher absorption and emittance of the defect relative to the surrounding material. Thus, the detection ability of a defect is enhanced by scanning with laser beam 24, and the transient response, as peak 64 decays back to about peak 62 (FIG. 2B), may be observed and analyzed to distinguish between a defect, which could cause a failure of the component, and other minor imperfections within the selected surface 18 of component 10.

In accordance with the present invention, a series of infrared images of surface 18 are recorded by VCR 54 and/or stored by CPU 48 at each scan location of cursor 61 to facilitate observation and analysis of the transient response as the radiance received from the defect decays from peak 64, at the moment the laser is radiating the defect, back to about its original intensity level, peak 62, at some time after laser scanning. The infrared images are converted to a graphical form, similar to FIGS. 2B and 2C, which collectively represent the transition or transient response of the radiance from the defect after laser scanning. The amount or degree of decay between the peaks of successive images over a selected time period may be analyzed to distinguish between a defect, which could result in a failure of the component, and other minor imperfections within the selected surface 18 of the component 10. The decay time for the transient response of a defect which could cause a failure of component 10 will typically be about 2 to about 4 times as long as a minor surface anomaly, depending upon the size of the defect or crack. Thus, the present invention is independent of the roughness of the component surface, and the transient response of the radiance from the surface under test may be analyzed to distinguish between a minor surface anomaly (as indicated by reference numeral 66 in FIG. 2C) and a defect (represented by peak 64 in FIG. 2C) which could cause a failure of component 10.

Radiative, or electromagnetic, heating is employed rather than conductive or convective heating, to utilize the higher absorptance (absorptance=emissivity) of the crack relative to the surface area surrounding the crack during radiative heating. A temperature difference will be created by the increased amount of energy absorbed in the crack relative to the surrounding surface area; this produces an enhanced signal-to-noise ratio (SNR) or contrast between the crack and surrounding surface area or background because the background reflects most of the power. Two separate effects contribute to the observed contrast: 1. an emissivity difference between the crack and the surrounding surface area which will cause a higher radiance from the crack at a selected constant temperature (the constant temperature may be ambient or the surface may be preheated as described hereinabove), and 2. an increase in temperature (delta T) of the crack relative to the surrounding surface which was caused by the choice of radiative heating, such as laser scanning, rather than conductive or convective heating. These two effects combine to give an improved SNR or contrast over either effect alone.

The intensity of the irradiance and the decay time of the transient response between peak 64 and peak 62 will be a function of the power of laser beam 24, because substantially more of the power of the laser beam will be absorbed by the defect or crack when beam 24 passes over the defect, and therefore the radiance of the crack will be substantially higher than the radiance of the surrounding material, which will reflect more of the laser beam energy.

One reason for the enhanced contrast between the defect or crack and the area of component 10 surrounding the crack is due to the higher signal-to-noise ratio (SNR) while the defect is under laser irradiation. The SNR value remains high immediately after scanning by the laser but decays back to the pre-laser scanning value at a given rate corresponding to the rate of decay of the intensity level of the radiance from the defect. Thus, the SNR value may also be used as a qualitative aid in identifying serious cracks or defects and discriminating between them and other background artifacts within the surface of the component.

Referring back to FIG. 1, in accordance with a further embodiment of the present invention, if the crack or defect is subsurface and proximate to the surface under inspection, a stress may be placed on component 10 by fixtures 12 and a mechanical stressing fixture 68 to open the crack so that it will be detectable at the component surface 18. Mechanical stressing fixtures are known and stressing fixture 68 will apply a force, in a direction indicated by arrow 70, to component 10 on a surface 72 opposite to surface 18 under inspection. Other methods for applying a stress to component 10 to cause a subsurface defect to open at surface 18 may be used as well, such as a stress applied to component 10 through fixtures 12 in the direction indicated by arrows 74 in FIG. 1. The stress or loading placed on component 10 should be at an intensity level below the characteristic damage threshold stress intensity level of the material from which the component is made; otherwise, severe damage could result to the component.

The present invention also provides superior results in the detection of fatigue cracks in the edges of bolt holes, rivet holes and the like because of the increased contrast in the infrared video signal generated due to the laser scanning and as a result of the analysis of the transient response of the irradiance during the laser scanning.

It will be readily understood by those skilled in the art that the present invention is not limited to the specific embodiments described and illustrated herein. Different embodiments and adaptations besides those shown herein and described, as well as many variations, modifications and equivalent arrangements will now be apparent or will be reasonably suggested by the foregoing specification and drawings, without departing from the substance or scope of the invention. While the present invention has been described herein in detail in relation to its preferred embodiments, it is to be understood that this disclosure is only illustrative and exemplary of the present invention and is made merely for purposes of providing a full and enabling disclosure of the invention. Accordingly, it is intended that the invention be limited only by the spirit and scope of the claims appended hereto.

What is claimed is:

1. A method for detecting a defect in a workpiece, comprising the steps of:
   (a) positioning a surface of the workpiece to be inspected in an optical path of an infrared radiation detector;
   (b) generating a graph of irradiance versus distance along a selected portion of the workpiece to establish an original irradiance intensity level;
   (c) heating the selected portion of the workpiece by electromagnetic radiation for a selected duration to cause an increase in radiance from any defect present at the workpiece surface in the selected portion, the radiation detector operating in a different spectral band than the electromagnetic radiation wherein any defect has a substantially higher emissivity relative to the workpiece surface surrounding the defect to cause an enhanced signal-to-noise ratio so as to allow distinction of a flaw which may cause a failure of the workpiece from another minor surface anomaly;
   (d) generating a series of graphs of irradiance versus distance along the selected portion as the irradiance decays from a peak intensity level back to the original intensity level after the heat is removed, the series of graphs representing a transient response of the irradiance from the selected portion; and
   (e) detecting defects in the selected portion of the workpiece by comparing the graphs to one another to analyze the transient response of the radiance received from the selected portion by the infrared radiation detector and to distinguish any flaw which may cause a failure of the workpiece from another minor surface anomaly.

2. The method of claim 1, wherein step (d) comprises the steps of:
   (d1) generating a series of images of the heated selected portion from the irradiance detected by the infrared radiation detector; and
   (d2) generating the series of graphs of irradiance versus distance along the selected portion from the images.

3. The method of claim 1, wherein step (c) comprises the step of focusing a laser beam on the selected portion.

4. The method of claim 3, wherein the laser beam is generated by a YAG laser operating at a wavelength of about 1.06 microns and the laser beam is substantially normally incident upon the selected portion.

5. The method of claim 1, wherein the radiation detector is an infrared imaging radiometer operating at a wavelength band between about 3 microns and about 12 microns.

6. The method of claim 1, further comprising the step of reducing an emissivity of the workpiece surface by cleaning the workpiece surface to remove any coatings.

7. The method of claim 1, further comprising the step of preheating the workpiece surface to a selected temperature before step (b).

8. The method of claim 7, wherein step (c) comprises the step of scanning the workpiece surface with a laser beam.

9. The method of claim 1, wherein step (e) further comprises the step of distinguishing a fatigue crack which may cause a failure of the workpiece from another minor surface anomaly by analyzing an intensity level of the irradiance during step (c) and a decay rate of the irradiance intensity level after removing the heat.

10. The method of claim 1, further comprising the step of applying a stress to the workpiece to cause any subsurface defects proximate to the surface under inspection to be detectable at the workpiece surface.

11. The method of claim 10, wherein the stress applied has an intensity level below a characteristic damage threshold stress intensity factor of a material from which the workpiece is made.

12. The method of claim 1, wherein the optical path is substantially parallel to the surface normal of the workpiece selected portion.

13. A method for detecting a fatigue crack in a component, comprising the steps of:
 (a) positioning a surface of the component to be inspected in an optical path of an infrared imaging radiometer;
 (b) generating a graph of irradiance versus distance along a selected portion of the surface to establish an original irradiance intensity level;
 (c) selectively heating the selected surface area of the component by scanning with a laser beam to cause an increase in radiance from the selected surface area, the infrared imaging radiometer operating in a different spectral band than the laser beam;
 (d) generating a series of video images of the heated surface area from the irradiance received by the infrared radiometer during and immediately after scanning with the laser beam;
 (e) generating a series of graphs of irradiance versus distance along the selected surface area from the video images, the graphs corresponding to a transient response of the irradiance during and immediately after scanning with the laser beam; and
 (f) distinguishing between a minor surface anomaly and a crack which may cause a failure of the component by analyzing an intensity level of the irradiance and a decay rate from a peak intensity level to the original irradiance intensity level after laser scanning, the decay rate for a crack which may cause a failure of the component being more than about 2 times as long as the decay time for a minor surface anomaly.

14. The method of claim 13, wherein the optical path is substantially parallel to the surface normal of the selected surface area.

15. The method of claim 13, wherein the laser beam is generated by a YAG laser operating at a wavelength of about 1.06 microns and the laser beam is substantially normally incident upon the selected surface area.

16. The method of claim 13, further comprising the step of preheating the workpiece surface to a selected temperature before step (b).

17. The method of claim 16, wherein the selected temperature is between about 50° C. and about 150° C.

18. The method of claim 13, further comprising the step of applying a stress to the component to cause any subsurface defects which are proximate to the surface to be detectable at the component surface.

19. An apparatus for detecting a crack in a component, comprising:
 means for generating a graph of irradiance versus distance along a selected surface area of the component to establish an original irradiance intensity level;
 means for heating the selected surface area of the component to cause an increase in radiance from any crack present at the component surface, wherein any crack which may cause a failure of the component has a substantially higher emissivity relative to the component surface surrounding the crack to cause an enhanced signal-to-noise ratio so as to allow distinction of any crack which may cause a failure from other minor surface anomalies;
 means for receiving the radiance from the selected surface area; and
 means for generating a series of graphs corresponding to the radiance received from the selected area immediately after heating as the irradiance decays from a peak intensity level back to said original intensity level, said series of graphs providing a transient response of the radiance received to distinguish between a minor surface anomaly and a crack which may cause a failure of the component.

20. The apparatus of claim 19, wherein said heating means comprises:
 a laser; and
 optical means for scanning the laser across the selected surface area.

21. The apparatus of claim 20, wherein said laser and said optical means are positioned to provide a laser beam which is substantially normally incident upon the selected surface area.

22. The apparatus of claim 19, wherein said radiance receiving means comprises an infrared imaging radiometer positioned in an optical path substantially parallel to the surface normal of the selected surface area.

23. The apparatus of claim 19, further comprising:
 means for generating at least one image of the irradiance from the selected surface area.

24. The apparatus of claim 23, further comprising:
 means for digitizing the at least one image to facilitate storage and analysis of the at least one image to distinguish between a minor surface anomaly and a crack which may cause a failure of the component.

25. The apparatus of claim 19, further comprising means for applying a stress to the component to cause any subsurface defects which are proximate to the surface to be detectable at the selected surface area, said stress having an intensity level below a characteristic damage threshold stress intensity factor of the component.

* * * * *